United States Patent [19]

Cannalonga et al.

[11] 3,959,472

[45] May 25, 1976

[54] FREE-FLOWING, HIGH DENSITY, AGGLOMERATED RIBOFLAVIN POWDERS

[75] Inventors: Marco Alfred Cannalonga, Fort Lee; Louis Vincent Czarecki, Succasunna, both of N.J.

[73] Assignee: Hoffmann-La Roche Inc., Nutley, N.J.

[22] Filed: June 26, 1974

[21] Appl. No.: 483,469

Related U.S. Application Data

[62] Division of Ser. No. 242,789, April 10, 1972, abandoned.

[52] U.S. Cl. .............................. 424/252; 424/254; 424/344
[51] Int. Cl.² ..................................... A61K 31/525
[58] Field of Search ..................................... 424/252

[56] References Cited

UNITED STATES PATENTS

| | | | |
|---|---|---|---|
| 2,974,087 | 3/1961 | Rogers | 424/252 |
| 3,446,899 | 5/1969 | Cavalli et al. | 424/252 |
| 3,608,083 | 9/1971 | Bunnell | 424/284 |

*Primary Examiner*—Norman A. Drezin
*Attorney, Agent, or Firm*—Samuel L. Welt; Bernard S. Leon; William M. Farley

[57] ABSTRACT

A novel spray-drying technique process, and the resulting composition, for preparing a high density, agglomerated vitamin-containing composition having improved tableting characteristics.

1 Claim, No Drawings

3,959,472

FREE-FLOWING, HIGH DENSITY, AGGLOMERATED RIBOFLAVIN POWDERS

This is a division of application Ser. No. 242,789 filed Apr. 10, 1972, and now abandoned.

BACKGROUND OF THE INVENTION

Spray dried agglomerated and densified products are often essential to provide free-flowing material having the physical characteristics necessary for direct compression tableting technique.

Heretofore, free-flowing powder materials were prepared by dusting dried powders with a suitable dusting agent to minimize the development of static electricity and thereby prevent sticking and blocking of the powder flow path. Examples of such dusting agents, which are well-known in the art, include starch, starch esters and silicic acid.

In addition, agglomeration could be achieved by various wet or dry techniques. For example, wet granulation includes both the rotating drum, extrusion techniques and instantizing apparatus.

The formation of free-flowing spray-dried high density agglomerates suitable for direct compression tablet manufacture was, heretofore, not achieved using spray-drying techniques. Spray-drying depends on rapid evaporation rates which are obtained through a high spray surface-to-mass ratio (i.e., fine particle-sized materials). However, if large particulates and agglomerates of the spray feed are formed during the passage through the drying zone, these semi-dried particles tend to adhere on the walls of the spray chamber and thereon accumulate large masses of a wet product. This is especially true when the spray droplets formed from vitamin E emulsions formulated with a gelatin base, vitamin $B_2$ slurry in a film-forming base and vitamin A emulsion prepared in either acacia or a gelatin base.

It is an object of this invention, therefore, to prepare free-flowing, high density coated agglomerated material suitable for direct compression into tablets using spray-drying techniques.

BRIEF DESCRIPTION OF THE INVENTION

This invention relates to a spray-drying process for preparing free-flowing high density agglomerates suitable for direct compression into tablets. It has been found that the introduction of ultra-fine (i.e., 2–15 microns) particle sized absorbents into the spray chamber leads to the formation of coated high density, free-flowing agglomerates which pass through the drying zone without the above described deleterious effects of wall adhesion and wet mass accumulation associated with prior art processes.

DETAILED DESCRIPTION OF THE INVENTION

Free-flowing high density agglomerates suitable for direct compression into tablets, prepared by the process of this invention, i.e., the introduction of ultra-fine particle-sized absorbents into the spray chamber, can be obtained by either of two modifications.

In the first modification the absorbents are metered directly into the spray chamber. The quantity of absorbent metered into the chamber ranges from about 1 to about 5% by weight based on the weight of the spray-dried product. The fine particle size absorbent immediately coats the semi-dried droplets as well as the chamber wall thus preventing buildup of material on the chamber wall and the consequent deleterious formation of large masses of wet product. In addition, the presence of the absorbent minimizes the development of static electricity both during the spray-drying step and on the resulting dry agglomerates.

In the second modification, a mixture of absorbent and previously fine particle-sized spray-dried material is directly metered into the spray chamber by a suitable valve arrangement. The mixture is immediately picked up by the high velocity air stream from the air disperser in the chamber and is intimately admixed with the atomized wet spray product, thereby forming coated agglomerates which dry readily. This second modification results in formation of large dried agglomerates when the metered admixture comprises from about 1 to about 15% by weight of the absorbent and from about 85 to about 99% by weight of the fine particle-sized spray-dried product. Examples of the fine particle-sized spray-dried materials include vitamin E encapsulated in hydrolyzed gelatin, vitamin A encapsulated in hydrolyzed gelatin, vitamin A encapsulated in gum acacia, vitamin D encapsulated in hydrolyzed gelatin, riboflavin encapsulated in maltrin and spray-dried stabilized calcium pantothenate.

The process claimed herein is, of course, limited to formulations which can be dried by spray-drying techniques. The preferred materials for use in this process are vitamin slurries or emulsions. Representative emulsions include vitamin A-hydrolyzed gelatin, riboflavin-maltrin and, in particular, a vitamin E-hydrolyzed gelatin emulsion as described in U.S. Pat. No. 3,608,083. (Ser. No. 734,540).

The preferred embodiment of this invention is the preparation of a free-flowing, high density agglomerated vitamin E product suitable for direct compression tableting techniques. Vitamin E comprises a group of natural substances known as tocopherols. They are fat soluble, closely related chemical compounds found in vegetable oils such as wheat germ oil, rice oil, soy bean oil and the like. α-Tocopherol has the greatest biological activity per unit weight while its isomers beta, gamma, delta, epsilon, zeta and eta-tocopherols have vitamin E activity to a lesser extent. The tocopherols and their esters such as tocopheryl acetate, tocopheryl palmitate, tocopheryl succinate and the like are normally water-insoluble and oily, waxy, or low melting, which properties make them unsuitable for certain pharmaceutical applications, particularly, those in which a powder is required, e.g., vitamin tablets and capsules. Any of these tocopherols, their esters or compounds convertible to either tocopherols or their esters are suitable for use in the process of this invention. However, in order to insure the desired stability of vitamin E activity in the final powder it is preferred to use tocopherol esters. Typical suitable esters are the acetate, palmitate, succinate and the like. The preferred ester used according to this invention is dl-α-tocopheryl acetate. Sufficient tocopheryl acetate is utilized to insure that the resulting spray-dried powders contain from about 40 to about 60% by weight of vitamin E, i.e., the amount of vitamin E activity present in the powder is that which would be present if the vitamin E activity is present as pure vitamin E.

The aforesaid tocopheryl esters are emulsified with a hydrolyzed gelatin having a 0 Bloom and a molecular weight range of from 9,000 to 11,000. The amount of hydrolyzed gelatin in the final powder generally varies from about 60 to about 40% by weight. A hydrolyzed gelatin which is representative of those suitable for use in this invention is, e.g., marketed by Croda Colloid. While this soluble protein is representative of the hydrolyzed gelatins useful herein, this invention is, of course, in no way limited to the use of a particular hydrolyzed gelatin.

The tocopheryl ester and hydrolyzed gelatin are emulsified by admixing a 45% hot hydrolyzed gelatin stock solution with a warm dl-α-tocopheryl acetate. The admixture is then homogenized by the rapid agitation of a Homo mixer. The resulting emulsion, diluted with water to about 45% solids to give a proper spray viscosity, has a particle size range in the dispersed phase of from below 1 micron to about 3 microns. In addition, other vitamin emulsions, i.e., those of vitamins A, $B_2$, D and various admixtures thereof prepared in gelatin or gum acacia bases and suitable for spray drying, can be used in the process as claimed in this invention.

One representative emulsion of vitamin A is constituted of 610 parts by weight of gelatin, 150 parts by weight of sucrose, 40 parts by weight of EMQ, 200 parts by weight of vitamin A palmitate and water, q.s. to make 40–50% solids emulsion.

Another representative example is a riboflavin emulsion constituted of 216 parts by weight of riboflavin, 80 parts by weight of oyster shell flour, 104 parts by weight of maltrin and 380 parts by weight of water.

These spray dryable emulsions and slurries can contain optional additives as may be desired. For example, since hydrolyzed gelatin solutions readily support microbiological growth, it is preferred to add preservatives to protect the emulsion during preparation and holding prior to spray drying. The preservatives are added to the water used to prepare the gelatin solutions so that a level of about 0.4 to about 0.6%, preferably about 0.5%, of, for example, sodium benzoate and about 0.15 to about 0.25%, preferably about 0.2%, of, for example, sorbic acid, result in a final 45% by weight hydrolyzed gelatin solution.

Of critical importance in the process claimed in this invention is the introduction of ultra-fine absorbents (i.e., glidants) into the spray chamber. These absorbents or glidants are, in the main, silicic acid, silicon dioxide or various silicates. However, materials other than these may be equally effective since it is not so much the chemical compositions of the absorbents but rather their physical properties which are critical to this process. To be effective, the absorbent must be substantially insoluble in cold water, resistant to wetting by water, have an appreciable capacity to absorb and/or adsorb water and oil (i.e., an oil absorption capacity of from about 150 to about 400 pounds per 100 pounds), free-flowing, do not develop static electricity, have a particle size range from about 2 microns to about 16 microns and have a surface area of from about 175 to about 360m²/gm. Suitable materials include silicic acid, silicas, alkali metal silicates, magnesium carbonate, kaolin clays, dicalcium phosphate, tricalcium phosphate and the like. Representative commercial materials include Syloid, Cab-O-Sil, Aerosil, Supernat, Santocel, Zealox and Polysilicic acid. The preferred material for the process of this invention is silicic acid, a white, amorphous powder, insoluble in water and having the emperical formula $SiO_2 \cdot x\ H_2O$.

Another critical factor in the process is the feed rate of the emulsion or slurry. In the usual spray-drying operation, the emulsion feed is so regulated as to form small particles which dry before hitting the walls of the dryer chamber. These small particles have poor tableting characteristics, however. By increasing the feed flow, i.e., flooding, larger particles can be formed. These particles, which are not dried before striking the walls of the dryer chamber, adhere on the walls and build up as a semi-solid plastic mass, a condition known as ringing. However, when a absorbent or glidant is added to the drying chamber, operation under flooding conditions produces the desired large particles which are then coated with absorbent, agglomerate and and dry. There is no wall adhesion and a free-flowing high-density, large particle-size product results.

In the process of this invention, an emulsion is spray dried using a standard Spray Drying Apparatus. Inlet and outlet temperatures are adjusted to an optimum and the emulsion is fed at a high feed rate through the atomizer into the Dryer Chamber. The absorbent is then metered into the chamber through a top inlet valve positioned above an atomizer wheel rotating at a fixed rpm. The flow rate of absorbent is adjusted to achieve a concentration of from about 1 to about 5% by weight based on the weight of the spray-dried product. As soon as the drying system is balanced, the atomizer wheel speed and the outlet temperature are lowered by increasing the feed rate of the emulsion over the atomizer wheel causing a flooding condition. These adjustments cause the atomized spray droplets to increase in size, remain in a thermoplastic state longer, agglomerate and densify. The semi-dried agglomerates are prevented from adhering to the drying chamber wall by the coating of the glidant on both the particle surface and the chamber wall.

The agglomerated vitamin E product prepared by the process of this invention can be used in many ways as, for example, directly in food premixes, in dry water dispersible preparations as dilutions for bulk sales using feed carriers and in the preparation of tablets. The product has a moisture content range of 1–5% by weight and a bulk density range of 25–32 pounds/ft³. A minimum of 95% of the material passes through a No. 20 U.S. standard sieve. From 75–100% of the particles have particle sizes of from 74 to 287 microns.

The vitamin E product has tableting properties which are essential for the manufacture of high potency coated and uncoated tablets by a direct compression procedure. Heretofore, such high potency vitamin E tablets were difficult to manufacture because of poor flow properties, sticking of the powder product to the tablet machine table, variations in tablet weights, soft tablets, laminating of tablets and cracking of coated tablets.

The following examples illustrate this invention.

EXAMPLE 1

This example illustrates the procedure for the preparation of a free-flowing, high density agglomerated formulation of vitamin E acetate suitable for direct compression to tablets.

One kilogram of sodium benzoate and 2 kilograms of sorbic acid are dissolved in 547 kilograms of distilled water by heating to 65°–70°C. 450 kilograms of hydrolyzed gelatin (Croda Colloid) are then added slowly with agitation. The agitation is continued for 2 hours with the slurry maintained at 70°–80°C. Agitation is then stopped and the temperature is maintained at 70°C. overnight to eliminate the air from the heavily foamed gelatin solution.

The hot hydrolyzed gelatin stock solution is transferred to a homogenizing kettle equipped with a Homo-Mixer. Rapid agitation is begun with the Homo-Mixer and 600 kilograms of dl-α-tocopheryl acetate, previously heated to 40°–50°C., is slowly added. Distilled water is added at this time if needed to insure proper pumping action of the Homo-Mixer during emulsification.

In operation the primary emulsion is cycled through a sonic homogenizer, e.g., Homo-Mixer, back to the emulsion kettle to check the emulsion microscopically for particle size distribution in the dispersed phase. When an emulsion of suitable dispersed particle size, i.e., 1–3 microns, is prepared, the solids concentration is adjusted to insure proper viscosity by the addition of sufficient distilled water to make the total used 740 kilograms. The emulsion is then passed through the sonic homogenizer into a suitable storage vessel.

The inlet temperature of a 14 foot Bowen Dryer is adjusted to 325°F. and the outlet temperature adjusted to 200°–210°F. The operation of the spray dryer is started using water. When the system is well balanced, the water is shut off and the vitamin E/hydrolyzed gelatin emulsion is fed to the Dryer. The atomizer wheel speed positioned below the absorbent inlet is set initially at 12,000–13,500 rpm and the flow rate of silicic acid glidant, metered into the Dryer through a top inlet valve, is adjusted to provide a glidant concentration approximately equal to 2–3% of the concentration of the spray-dried product. The atomizer wheel speed is then adjusted downward to 8,000–9,000 rpm and, after five minutes, the Dryer outlet temperature is adjusted to 195°–180°F. By these adjustments, the emulsion feed rate is increased causing the spray droplets to increase in size and agglomerate. The wet agglomerate particles are coated with the glidant prior to impinging on the drying chamber wall. There is no adhesion and thus the thermoplastic particles have a long drying period.

In operation, it is often necessary to adjust the aforesaid drying conditions to optimize the physical properties (density, particle size distribution) of the agglomerated spray-dried product.

The resulting material is a white, free-flowing powder having a bulk density of 25–30 pounds per cubic foot and a moisture content of 1.0–4% by weight.

The agglomerates have the following typical particle-sized distribution:

| U.S. Standard Mesh | % Retained |
|---|---|
| On 60 mesh | 14.0–40.0 |
| On 80 mesh | 22.0–28.0 |
| On 100 mesh | 7.2– 7.0 |
| On 200 mesh | 30.4–17.5 |
| Through 200 mesh | 26.4– 7.5 |

To show the significant improvement achieved by the use of this free-flowing, high-density, agglomerated product in comparison to material prepared by the standard spray-drying techniques, the following vitamin E chewable tablet (200 IV/tablet) and vitamin E sugar coated tablet (200 IV/tablet) formulations were evaluated using direct compression techniques.

| | Formulation (mg./tablet) | |
|---|---|---|
| | Chewable | Sugar Coated |
| Vitamin E acetate, 50% spray-dried | 400 | 400 |

-continued

| | Formulation (mg./tablet) | |
|---|---|---|
| | Chewable | Sugar Coated |
| Cocoa | 22 | — |
| Silicic Acid | 35 | 50 |
| Sugar Tab | 311.5 | — |

The results are tabulated below:

| A. Chewable Formulations | | |
|---|---|---|
| | Standard Spray-Dried | Agglomerated Spray-Dried |
| Tableting Characteristics | Poor Flow Laminating of Tablets Sticking to Machine Table | Good Flow No Lamination No Sticking |
| Tablet Hardness (Strong Cobb Units, SCU) | Capping to 5 | 12–24 |
| B. Sugar-Coated Formulations | | |
| | Standard Spray-Dried | Agglomerated Spray-Dried |
| Tableting Characteristics | Capping Not suitable for tablets | Excellent |
| Tablet Hardness (Strong Cobb Units, SCU) | No tablets | 20–25 |

EXAMPLE 2

This example illustrates the procedure for the preparation of free-flowing, high density, agglomerated formulation of an agricultural dry vitamin A palmitate, potency 325,000 vitamin A units per gram.

610 Kilograms of low Bloom hydrolyzed gelatin are added slowly with agitation to 610 kilograms of distilled water heated to 65°–70°C. The agitation is continued for 2 hours with the slurry maintained at 70°–80°C. Agitation is then stopped and the temperature is maintained at 70°C. overnight to eliminate the air from the heavily foamed gelatin solution.

The hot hydrolyzed gelatin stock solution is transferred to a homogenizing kettle equipped with a Homo-Mixer. Rapid agitation is begun with the Homo-Mixer and a mixture of 200 kilograms of vitamin A palmitate and 40 kilogram EMQ (1,2-dihydroxy-6-ethoxy-2,2,4-trimethylquinoline) previously heated to 40°–50°C. is slowly emulsified. 150 kilograms of sucrose are slowly added to the emulsion with continued agitation. Distilled water is added at this time if needed to insure proper pumping action of the Homo-Mixer during emulsification.

In operation the primary emulsion is cycled through a sonic homogenizer to insure the preparation of an emulsion with suitable dispersed particle size, i.e., less than 1–3 microns. The solids concentration is adjusted to insure proper viscosity by the addition of sufficient distilled water to reduce the total solids content of the emulsion to 40–45%. The emulsion is then passed through the sonic homogenizer into a suitable storage vessel.

The inlet temperature of a 14 foot Bowen Dryer is adjusted to 400°F. and the outlet temperature adjusted to 270°–280°F. The operation of the spray dryer is started using water. When the system is well balanced, the water is shut off and the vitamin A-antioxidant-hydrolyzed gelatin emulsion is fed to the Dryer. The atomizer wheel speed positioned below the absorbent inlet is set initially at 12,000–13,500 rpm and the flow rate of silicic acid absorbent-glidant, metered into the Dryer through a top inlet valve, is adjusted to provide a glidant concentration approximately equal to 2–3% of the concentration of the spray-dried product. The atomizer wheel speed is then adjusted downward to 8,000–9,000 rpm and after 5 minutes, the Dryer outlet temperature is adjusted to 255°–245°F. By these adjustments, the emulsion feed rate is increased causing the spray droplets to increase in size and agglomerate. The wet agglomerate particles are coated with the glidant prior to impinging on the dryer chamber wall. There is no adhesion and thus the thermoplastic particles have a longer drying period.

In operation, it is often necessary to adjust the aforesaid drying conditions to optimize the physical properties (density, particle size distribution) of the agglomerated spray-dried product.

The resulting material is a tan, free flowing-powder having a bulk density of 35–45 pounds per cubic foot and a moisture content of 1 to 5% by weight.

The agglomerates are free-flowing and have enhanced stability compared to regular spray-dried powders.

EXAMPLE 3

This example illustrates a procedure for the preparation of free-flowing, high density, agglomerated, nondusting, static-free riboflavin, 50% using a slurry as the feed material for the Spray Dryer.

104 Kilograms of Maltrin 15, a hydrolyzed cereal product, are dissolved in 380 kilograms of water. 80 kilograms of oyster shell flour are then added with rapid agitation followed by 216 kilograms of riboflavin. The resulting slurry has a 51.32% solids content.

The inlet temperature of a 14 foot Bowen Dryer is adjusted to 350°F. and the outlet temperature adjusted to 225°–235°F. The operation of the spray dryer is started using water. When the system is well balanced, the water is shut off and the riboflavin slurry is fed to the Dryer. The atomizer wheel speed positioned below the absorbent inlet is set initially at 12,000–13,500 rpm and the flow rate of silicic acid glidant, metered into the Dryer through a top inlet valve, is adjusted to provide a glidant concentration approximately equal to 2–3% of the concentration of the spray-dried product. The atomizer wheel speed is then adjusted downward to 8,000–9,000 rpm and after 5 minutes, the Dryer outlet temperature is adjusted to 220°–205°F. By these adjustments, the emulsion feed rate is increased causing the spray droplets to increase in size and agglomerate. The wet agglomerate particles are coated with the glidant prior to impinging on the dryer chamber wall. There is no adhesion and thus the thermoplastic particles have a longer drying period.

In operation, it is often necessary to adjust the aforesaid drying conditions to optimize the physical properties (density, particle size distribution) of the agglomerated spray-dried product.

The resulting material is a brown, free-flowing, nondusting, static-free powder having a bulk density of 35–36 pounds per cubic foot and a moisture content of 4–5% by weight.

The agglomerates are free-flowing and, from the viewpoint of direct usage in premix operation are dust-free, and nonstatic with good particle size distribution.

EXAMPLE 4

This example illustrates the procedure for the preparation of an agglomerated formulation of dry vitamin E acetate using a mixture of ultrafine absorbent and previously spray-dried material as the absorbent feed.

A 200 gallon, jacketed Pfaudler kettle is charged with 50 gallons of distilled water, 1.75 kilograms of sodium benzoate and 0.7 kilogram of sorbic acid and heated to 65°–75°C. 153 kilogram of hydrolyzed gelatin (0 Bloom and molecular weight of 7,000–11,000) are slowly added with constant agitation. 30 kilograms of warm (35°–40°C.) dl-α-tocopheryl acetate are slowly added to 50 kilograms of the hydrolyzed gelatin solution at 50°–60°C. with stirring using a Homo-Rod Mixer until emulsification is complete. Sufficient distilled water is then added to reach about a 45% solids emulsion which provides a proper spraying viscosity.

The emulsion is then spray dried using a 14 foot Bowen Dryer with an inlet temperature of about 325°–350°F. and an outlet temperature of about 210°–225°F. The resulting product is white, has particles in the range of from about 20 to about 30 microns, a bulk density of about 18.5 pounds per cubic foot and a moisture content of about 1%.

This finely spray-dried vitamin E, 50% is intimately mixed with 4–12% of Micro-Cel C absorbent. Micro-Cel C is calcium silicate having an average particle size of 3.4 microns, an oil absorption capacity of 100–300 lbs./100 lbs. and a surface area of 175 $m^2$/gram.

Another emulsion, constituted as described in Example 1 above, is then prepared for spray drying. The 14 foot Bowen Dryer is set up for cyclone collection. Operation is started using water as the feed with the initial inlet temperature set at 325°F. and the initial outlet temperature set at 210°F. When the system is balanced, the feed water is replaced by the vitamin E emulsion. As the same time, the atomizer wheel speed is adjusted initially to 11,000–13,500 rpm. The top inlet feeder is adjusted to permit a flow rate of the admixture of Micro-Cel C absorbent and finely spray-dried vitamin E, 50% so as to provide a concentration approximately equal to 1–2% of the concentration of the spray-dried product. The atomizer wheel speed is adjusted downward to 8,000 to 11,000 rpm. After 5 minutes the outlet temperature is also adjusted downward to 195°–180°F., thus increasing the feed rate to flooding condition which results in the formation of large particle size droplets. These wet atomized particles of vitamin E emulsion collide with the dried particles of adsorbent and vitamin E/hydrolyzed gelatin to form large agglomerates coated with the adsorbent which are easily dried and collected. The moisture content, bulk density and particle size range are the same as reported for the agglomerated material in Example 1 above.

EXAMPLE 5

This example illustrates the procedure for the preparation of a free-flowing, high density, agglomerated flavor oil encapsulated powder.

610 Kilograms of low bloom hydrolyzed gelatin are added slowly with agitation to 610 kilograms of distilled water heated to 65°–75°C. The agitation is continued for 2 hours with the slurry maintained at 70°–80°C. Agitation is then stopped and the temperature is maintained at 70°C. overnight to eliminate the air from the heavily foamed gelatin solution.

The hot hydrolyzed gelatin stock solution is transferred to a homogenizing kettle equipped with a Homo-Mixer. Rapid agitation is begun with the Homo-Mixer and 152.2 kilograms of a flavor oil (e.g., orange oil, grape flavor, pineapple flavor), previously heated to 40°–50°C., is slowly added and emulsified.

The emulsion is cycled through the sonic homogenizer to prepare an emulsion with suitable dispersed particle size, i.e., less than 1–3 microns. The solids concentration is adjusted to insure proper spray viscosity, i.e., about 180–200 centipoises per second, by the addition of sufficient distilled water. The emulsion is then passed through the sonic homogenizer into a suitable storage vessel.

The inlet temperature of a 14 foot Bowen Dryer is adjusted to 325°F. and the outlet temperature adjusted to 200°–210°F. The system is balanced using water after which the water is shut off and the flavor oil-hydrolyzed gelatin emulsion is fed to the Dryer. The atomizer wheel speed positioned below the absorbent inlet is set initially at 12,000–13,500 rpm and the flow rate of silicic acid absorbent-glidant, metered into the Dryer through a top inlet valve, is adjusted to provide a glidant concentration approximately equal to 2% by weight of the concentration of the spray-dried product.

The atomizer wheel speed is then adjusted downward to 8,000–9,000 rpm and, after 5 minutes, the Dryer outlet temperature is adjusted to 195°–180°F. By these adjustments, the emulsion feed rate is increased causing the spray droplets to increase in size and agglomerate. The wet agglomerate particles are coated with the glidant prior to impinging on the Dryer chamber wall. There is no adhesion and thus the thermoplastic particles have a long drying period.

The resulting material is an agglomerated, free-flowing, flavor oil encapsulated powder having a bulk density of 35.4 pounds per cubic foot and a moisture content of 1.5 to 2.5% by weight.

We claim:

1. A spray-dried, free-flowing, non-dusting, static-free riboflavin powder composition comprising, in percents by weight based on the total weight of the powder, from about 45 to about 65% of riboflavin, from about 15 to about 25% of oyster shell flour as a non-absorbent inorganic filler, from about 15 to about 35% of a hydrolyzed cereal flour and from about 1 to about 5% of silicic acid; said composition in the form of agglomerated particles having a bulk density of 35–36 pounds per cubic foot.

* * * * *